United States Patent [19]
Winkler

[11] Patent Number: 5,376,125
[45] Date of Patent: Dec. 27, 1994

[54] HIP JOINT ENDOPROSTHESIS

[76] Inventor: Heinz Winkler, Oberlaaerstrasse 314, A-1232 Vienna, Austria

[21] Appl. No.: 90,093
[22] PCT Filed: Dec. 23, 1991
[86] PCT No.: PCT/AT91/00139
§ 371 Date: Jul. 23, 1993
§ 102(e) Date: Jul. 23, 1993
[87] PCT Pub. No.: WO92/12691
PCT Pub. Date: Aug. 6, 1992

[30] Foreign Application Priority Data
Jan. 25, 1991 [AT] Austria ................................. 167/91

[51] Int. Cl.⁵ .............................................. A61F 2/28
[52] U.S. Cl. ........................................ 623/23; 623/22
[58] Field of Search ...................... 623/16, 18, 19, 20, 623/22, 23

[56] References Cited
U.S. PATENT DOCUMENTS

| | | | |
|---|---|---|---|
| 2,668,531 | 2/1954 | Haboush | 623/22 |
| 2,682,265 | 6/1954 | Collison | 623/23 |
| 3,740,769 | 6/1973 | Haboush | 623/22 |

FOREIGN PATENT DOCUMENTS

| | | | |
|---|---|---|---|
| 0382395 | 8/1990 | European Pat. Off. | 623/23 |
| 2250501 | 5/1974 | Germany | 623/22 |
| 3538346 | 5/1987 | Germany | 623/23 |
| 2166359 | 5/1986 | United Kingdom | 623/23 |

*Primary Examiner*—David Isabella
*Attorney, Agent, or Firm*—Townsend and Townsend Khourie and Crew

[57] ABSTRACT

An endoprosthesis for a hip joint includes an acetabular implant and a femoral implant. The acetabular implant has a socket with a socket opening intersecting the rim of the socket in a plane. At least two tubular guides for positioning at the cranial region of the bone are attached to and laterally offset from the socket opening, have axes perpendicular to the socket plane, and slidingly receive attachment screws the ends of which are threaded into the bone. The femoral implant has a spherical head movably positioned in the acetabular socket which is mounted to an attachment member the distal side of which has a conical attachment surface bearing against the resected femoral neck. A sliding rod extends coaxially with the femoral neck axis laterally and distally into a sleeve connected to a plate which is secured to the femur.

4 Claims, 1 Drawing Sheet

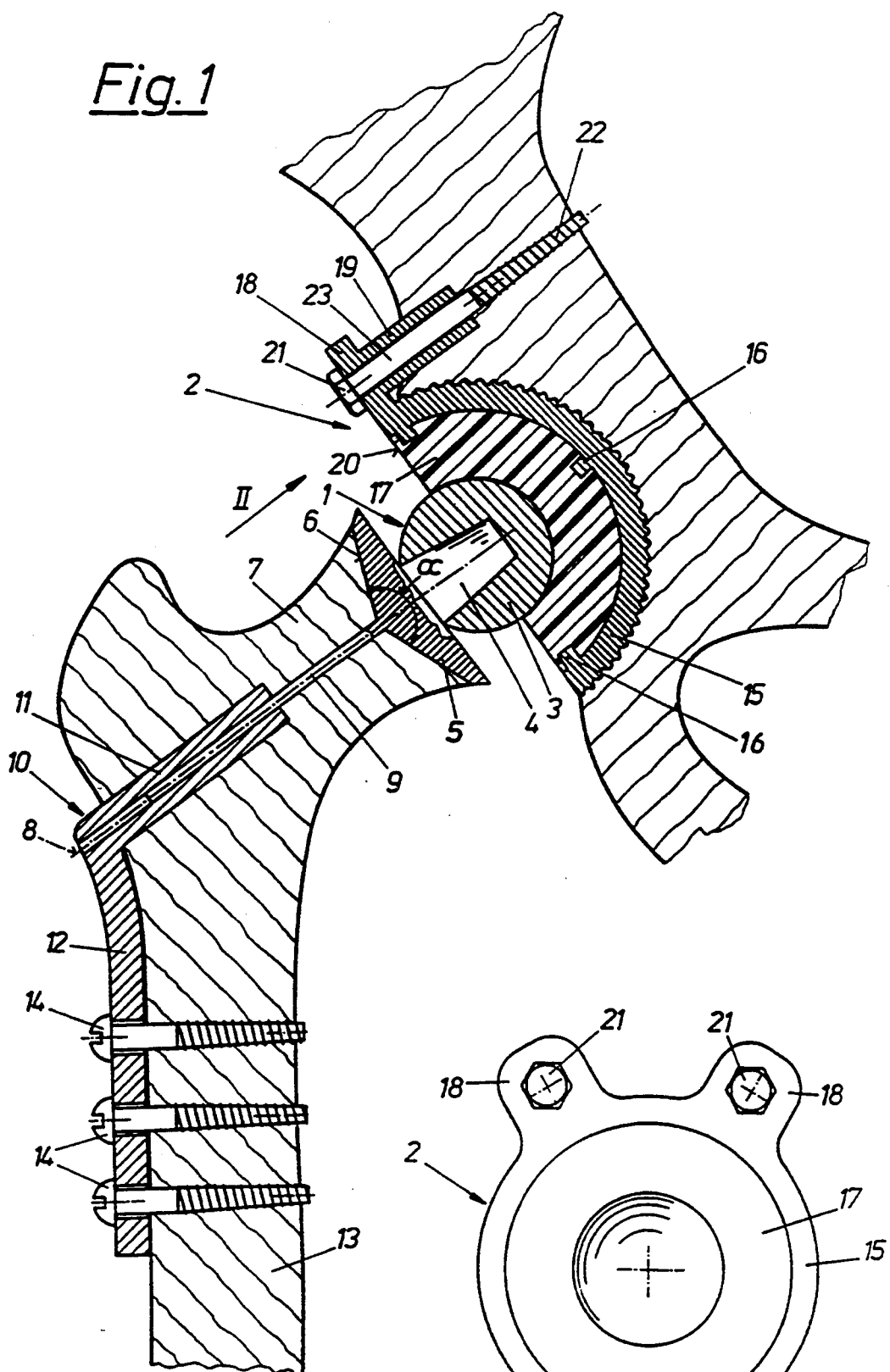

HIP JOINT ENDOPROSTHESIS

BACKGROUND OF THE INVENTION

The invention relates to an endoprosthesis, in particular for a hip joint, having an anchoring component which can be anchored to the bone and which is connected to a joint component. Endprostheses are implanted when a satisfactory therapeutic effect can no longer be achieved by operations performed to preserve the joint. This is particularly the case where hip joints are concerned when advanced arthropathy, necrosis of the head of the femur or a medial fracture of the neck of the femur are present.

One disadvantage of all known endoprostheses is that, although these are initially immovably joined with the bone, they can become loose after a certain amount of time. Living bone is constantly undergoing changes which may vary considerably from location to location. If, in the course of such changes, individual sections of the bone should become weakened in the peripheral area of the prosthesis, the bone at this point will give way and the prosthesis will move. Even if such movements occur only in the micro-range, the original stability is no longer guaranteed. Under unstable conditions, the force flows and load distributions on the bone are constantly changing and the bone cannot start any reparative reactions because the conditions for oriented growth are lacking. Instead, at the points where excessive stress builds up (stress reaction) the bone will react by locally atrophying as it does at points where the stress is too low (stress protection). This leads to a progressive loosening of the prosthesis.

Such restructuring of the bone must be expected to occur even years after the prosthesis has successfully healed into place, because bone is a living organ and it reacts to changes in lifestyle, diet and other circumstances. Conventional endoprostheses do not take account of this situation.

A loosening process of this kind is one of the major problems encountered in orthopaedic surgery and it frequently necessitates replacement of the prosthesis. The corrective operations required in this case are, however, much more problem-ridden than the primary interventions because not only is the bone tissue which was removed for the primary implantation now missing, but also usually as a result of the interventions because not only is the bone tissue which was removed for the primary implantation now missing, but also usually as a result of the loosened implant or because of the resulting abrasion, additional serious defects are created which make it extremely difficult or indeed impossible to re-fix the implant.

In the case of hip endoprostheses sometimes only the head and neck of the femur are removed and replaced by a head prosthesis.

In the prior art head prostheses the anchoring component consists usually of a metal spike, for example of titanium, which is fixed in the medullary cavity of the femur and it is fitted with a laterally projecting pin whose free end bears a head section. In order to implant such a prosthesis it is necessary to remove the head and neck of the femur as well as most of the sponglous bone at the proximal end of the femur. The spike is then cemented into the femoral medullary cavity using polymethylmethacrylate, or it is driven into the bone without any cement; in this latter case it is primarily necessary to achieve optimal contact between the bone and the implant, and this may be reinforced by secondary growth of new bone tissue.

German Patent Application DE-A 28 45 231 describes a joint prosthesis in which a joint component is provided with a shaft which is attached to the bone by means of a tension bolt.

German Patent Application DE-A 28 54 334 describes an endoprosthesis of complicated design for a hip joint. The prosthesis consists of a shaft running longitudinally in the medullary cavity of the bone, and a neck part running in the direction of the neck of the femur and carrying the head of the joint. In this design, the shaft in the medullary cavity is rigidly connected to the femoral neck part.

German Patent Application DE-A 30 17 953 reveals an endoprosthesis for the head of a femur in which the head component is rigidly and non-slidingly connected via a threaded bolt with an anchoring component consisting of a sleeve inserted into the bone and of a trochanteral plate bolted to the outer surface of the bone. In this case the threaded bolt acts as a tension anchor by means of which the prosthesis is pretensioned against the bone.

German Patent Application DE-A 34 20 035 describes a joint prosthesis in which the head of the joint is rigidly attached to the bone via a projecting member.

One common feature of all these prior art joint prostheses is that they are non-flexibly attached to the bone in a manner which does not allow for later restructuring processes taking place in the bone.

When an acetabular prosthesis is implanted, still intact bone material is sometimes removed from the pelvic bone in order to be able to cement the socket into place or to anchor it in position without the use of cement. This known method of carrying out the operation, using known types of endoprosthesis, has a number of disadvantages. For example, large amounts of intact bone material have to be sacrificed, including in particular those parts of the bone in the proximal area of the femur which, because of their ideal trajectory, provide for optimum absorption of forces.

In the area of the femoral shaft, the existing force flows are reoriented. Under natural conditions, mainly pure bending stresses, harmoniously distributed from top to bottom, predominate in this area, but when the prosthesis has been implanted forces are generated which run mainly from inside the bone to the outside and these are combined with shear forces and a relatively abrupt transition from low stress in the portions of the bone in contact with the prosthesis to extreme stress at the lower tip of the anchoring spike. The bone itself is forced to react to the changed conditions by undergoing restructuring. This applies not only to the femoral but also to the acetabular conditions. Restructuring always involves the simultaneous loss of existing bone and the growth of new bone. If the amount of bone lost exceeds the amount of new bone growth, the prosthesis will lose its grip in certain sections and it will start to come loose.

Also, when the prior art hip joint prostheses are used, insufficient attention is paid to the individually different conditions in the patient's anatomy. For example, the angle between the shaft and the neck of the femur ("CCD angle") varies in size from person to person (the physiological range is taken to be 115° to 140° degrees). Furthermore, the neck of the femur does not run in the sagittal plane of the body but is tilted forward and towards this plane at an angle of varying size ("AT angle", physiological range approx. 10° to 40° degrees). The sizes of both angles are proportionately interdependent. Prior art endoprostheses do not take these facts into account and only one standard dimension is used for all hips. As a result, this almost always leads to functionally incorrect placing of the joint and consequently also a change in the way in which forces are introduced into the shaft of the femur. To the extent that they are capable, bones and soft tissues must adapt to the new conditions. Pain, restricted mobility and premature loosening of the prosthesis are all possible consequences. Custom-made prostheses are not immediately available, they are for the most part inaccurate, and they cost up to ten times as much. Furthermore, computer tomography, which exposes the patient to large amounts of radiation, is needed to determine the anatomical situation prior to performing the operation. In this case, too, the functionally incorrect siting of the joint involves the risk that the implanted prosthesis will come loose, with all the disadvantages already mentioned above.

Colonization of the surface of the prosthesis by bacteria is a not infrequent and much feared complication following implantation. Such contamination usually makes it necessary to remove the prosthesis completely. However, removing an endoprosthesis which has become firmly interlocked with the bone growing around it, or removing the bone cement, is a very difficult task which frequently results in severe additional damage to the surrounding bone structures. Replacing the prosthesis with a new one cannot be done at all or only after the bone has been allowed to heal for several years. If an infection exists in the area of a femoral head prosthesis of prior art design, then because the prosthesis is anchored in the medullary cavity of the femur it must be expected that the infection will spread as far as the knee joint.

Anchoring the head component of the prosthesis in the shaft of the bone is not only a non-physiological approach but also it is not always technically simple to accomplish. Usually, an extensive set of additional surgical instruments is needed to prepare the bone in the exact manner required. Furthermore, opening up the medullary cavity always results in heavy and persistent bleeding which necessitates the administration of multiple units of stored blood.

SUMMARY OF THE INVENTION

It is a purpose of the present invention to avoid the aforementioned disadvantages and to create an endoprosthesis which is able to adapt itself in a controlled manner, in particular to any changes which may occur at a later date in the bone. To solve this task in the manner according to the invention it is proposed that, proceeding from an endoprosthesis of the type described at the beginning, either the anchoring component or the joint component should possess a tubular guide, and that the other one of these two components should possess a rod-shaped sliding component which is slidingly mounted in the tubular guide, in the path of the physiological force flow. The design of the endoprosthesis according to the invention thus guarantees the guided sliding motion of the joint component relative to the anchoring component, namely in an exactly predetermined axial direction, i.e. the direction of flow of the physiological forces, throughout the entire period of time that the endoprosthesis is in use. This offers two main advantages. On the one hand, the guided sliding motion permits axial displacement in the event that localized bone loss occurs, so that the prosthesis remains stable over a practically unlimited period of time following implantation; in contrast, when the prior art prostheses are used, there is a risk that, because of restructuring processes taking place in the living bone after the prosthesis has healed into place, the said prosthesis will become loosened or no longer optimally positioned; on the other hand, the arrangement according to the invention offers the further advantage that the prosthesis automatically adjusts itself to the optimum position, thereby ensuring an optimum distribution of the load between the prosthesis and the bone. In the design according to the invention, the anchoring component plays only a subordinate role in absorbing the force flows. Instead, as in the natural joint, the forces flow through the preformed bone structures.

The head prosthesis according to the invention, which consists of an anchoring component attached to the femur and joined via a neck component to a head component attached thereto, is characterized in that the neck component is connected to the rod-shaped sliding component which is slidingly arranged, substantially along the axis of the femoral neck, in a tubular guide connected to the anchoring component, and the sliding component is provided with an attachment bearing on the neck of the femur. This ensures that a physiologically correct force flow is created, so that even after the prosthesis has been implanted the forces are naturally distributed in the femur and no individual section of the bone is subjected to non-physiological load stresses to which it reacts by undergoing restructuring.

At the same time, the attachment element provides reliable anchoring of the prosthesis to the femur without it being necessary to remove large amounts of intact bone material.

In accordance with a preferred embodiment of the invention, the surface of the attachment bearing on the neck of the femur has the form of a truncated cone, the vertex of the cone has a lateral-distal orientation, and the axis of the cone coincides with the axis of the rod-shaped sliding component. The vertex angle of the cone is advantageously between 135° and 140°. This ensures that the surfaces of the attachment in contact with the bone are everywhere substantially perpendicular to the preformed trabecular structures. This also guarantees that the anatomically predetermined ratios between the CCD and AT angles are retained after the prosthesis has been fitted. The forces are therefore transmitted in a substantially physiologically correct manner over the naturally existing structures.

In accordance with a further feature of the invention, the neck component possesses a cone element arranged centrally to the truncated conical attachment; the axis of this cone element coincides substantially with the axis of the femoral neck and the cone is inserted into a conical recess in the head component of the prosthesis. By means of this design it is possible to use head components from prior art prostheses in the endoprosthesis according to the invention, i.e. this latter endoprosthesis can be combined with prior art types of head components.

In accordance with a preferred embodiment of the invention, the anchoring component possesses a plate of known design, for use with dynamic hip screws, which is attached laterally to the femur. This plate is connected to the tubular guide which passes through the neck of the femur in a substantially axial direction and in which the sliding component is slidingly located. With this arrangement, it is not necessary to remove large portions of still intact bone material, thus the amounts of bone sacrificed in the previously known types of endoprosthesis are for the most part saved. All that is necessary is to arrange a borehole in the axis of the femoral neck, through which the sleeve can be inserted. The anchoring component is fixed in position by laterally screwing the plate to the bone, thus obviating the need for laborious preparation of the femur using a complex set of instruments. Because the anchoring component is not anchored in the medullary cavity of the femur, persistent bleeding from that cavity is avoided and the need for blood transfusions is considerably reduced, indeed, they may not be necessary at all. If bacteria infect the area, the anchoring component can easily be removed and it is not possible for an infection process to spread over the entire femur, consequently immediate reimplantation of a new prosthesis is a much less risky procedure. This design offers the further advantage that if the endoprosthesis according to the invention should ever fail, it can be replaced without any problem by a prior art type of prosthesis as if the operation were being performed for the first time, because the implantation according to the invention does not create any defects in the needed bone substance.

The acetabular prosthesis according to the invention is based on a known type of socket anchored in a recess cut out of the pelvic bone and having at its cranial margin at least one bracket which can be attached to the pelvic bone by fastening devices. The said acetabular prosthesis is characterized in that at least two tubular guides connected with the bracket or brackets are provided, with their axes running perpendicular to the plane of the socket opening, and through these guides pass screws having rod-shaped sections slidingly arranged relative to the tubular guides, which can be anchored in the pelvic bone. This design also ensures that, if the bone structure undergoes any changes, the sliding mounting can permit axial displacement of the socket without allowing the latter to tilt or rotate, so that even in cases of localized bone loss, the prosthesis remains stable at all times, without the flow of forces between the prothesis and the bone being disrupted or interrupted. Even if the prosthesis should undergo any settling, all the circumferential parts of the socket continue to be uniformly loaded. In contrast, in the known types of prosthesis there is a risk of tilting occurring, which would interfere with the flow of forces. Furthermore, once the screws have been inserted, this design permits the socket to be displaced perpendicularly to the plane of the socket opening, however at the same time it prevents the socket from tilting or rotating.

In order to ensure that the thread of the screws does not prevent the sliding motion in the axis of the screws, the latter—in accordance with a further feature of the invention—possess a central threaded anchoring section and a peripheral sliding section slidingly mounted in the associated sleeve.

When preparing the bed in the bone for the acetabular prosthesis according to the invention, it is no longer necessary as in the past to remove all the sclerotic portions of bone or even to create additional defects such as a conical or threaded preparation of the bone, instead it is sufficient to prepare a congruent hemispherical cavity using conventional rasps and to remove any remaining fragments of cartilage, because inhomogeneities in the bone structure can be balanced out again thanks to the self-regulating characteristic of the acetabular prosthesis according to the invention. In this case, also, the sacrifice of still intact bone material is reduced to an absolute minimum.

BRIEF DESCRIPTION OF THE DRAWINGS

FIG. 1 shows a complete endoprosthesis for a hip joint; and

FIG. 2 shows a view of the acetabular prosthesis seen in the direction of the arrow II in FIG. 1.

DESCRIPTION OF THE PREFERRED EMBODIMENTS

The complete hip endoprosthesis illustrated here possesses a head prosthesis 1 and an acetabular prosthesis 2.

The head prosthesis 1 consists of a head component 3 mounted on a cone 4 which is connected to an attachment 5 having a truncated conical surface 6 which rests in a recess cut into the neck of the femur 7. The vertex of the truncated cone is thus laterally and distally oriented and the axis of the truncated cone coincides substantially with the axis 8 of the femoral neck 7.

The vertex angle a of the truncated cone is between approximately 135° and 140°, so that the surface 6 of the attachment 5 lies approximately perpendicular to the preformed trabecular structures.

The cone 4 and the attachment 5 together form a neck component which is connected to a rod-shaped sliding part 9 emerging from the vertex of the truncated cone and slidingly guided along the axis of the femoral neck 8 in an anchoring component 10. For this purpose, the anchoring component 10 possesses a sleeve 11 which is inserted into a laterally-distally open borehole in the neck of the femur 7 and oriented along the axis of the neck of the femur. The sleeve 11 is connected to a plate 12 provided with holes through which screws 14 are passed and then screwed into the femur 13.

The acetabular prosthesis 2 consists of a hemispherical socket 15 made of a highly biocompatible metal such as titanium, and it is provided with customary fastening devices 16 for securely inserting an inlay 17 made of slippery material, for example polyethylene. As can be seen from FIG. 2, the socket 15 is connected at its cranial margin to two brackets 18, each of which is fitted with a sliding sleeve 19, and the axes of these sliding sleeves run perpendicular to the plane of the socket opening 20. However, each bracket 18 may also possess two or more sliding sleeves 19 through which pass screws 21, and it is possible also to provide just one bracket with at least two sliding sleeves 19. After the socket 15 has been implanted, it is fixed in place in the acetabulum by means of the screws 21 passing through the sliding sleeves 19. The screws 21 possess a central threaded anchoring section 22 and a peripheral sliding section 23 which is slidingly located in the sleeves 19.

This arrangement guarantees that the socket 15 is fixed so as to prevent it from tilting and rotating but, because the axes of the screws are perpendicular to the plane of the socket opening 20, it also permits axial displacement in the event of localized loss of bone and thus the stability of the prosthesis is maintained.

The following procedure is followed when implanting the complete endoprosthesis as shown in the drawing:

Once the joint capsule has been opened up and following luxation of the head section of the hip, the latter is resected at the cartilage-bone interface, ensuring that the resection plane remains as closely as possible perpendicular to the axis of the femoral head 8. In the case of a medial fracture of the neck of the femur, the broken head is first removed and then only the larger cortical splinters are smoothed down in the area of the neck stump. Next, starting from the resection surface, a drill guide wire is centrally positioned along the axis of the neck of the femur 8. The wire passes through the entire neck section 7 and emerges laterally from the femur 13. The central position of the wire can be ensured by using an aiming device or by carrying out X-ray monitoring (image converter). Subsequently, drilling is carried out using a multi-cut drill bit, starting laterally and moving along the length of the wire. In this way a borehole of large diameter is produced for the sleeve 11 of the anchoring component 10 and a borehole of smaller diameter is produced to accept the sliding component 9. The angle between the borehole and the shaft of the femur is measured and the anchoring component 10 is selected in accordance with this angle; it is then inserted and attached by screws 14 to the femur 13. Next, the bearing surface for the attachment 5 is prepared from the medial end using a rasp of truncated conical shape corresponding exactly to the shape of the attachment 5 and having at its vertex a guide rod which is introduced into the already inserted sleeve 11. The preparation process continues until all the cortical edges of the neck stump of the femur have been smoothed down.

The bed for the joint socket is prepared using a conventional hemispherical rasp whose diameter should correspond to the maximum diameter of the acetabulum. A test socket of identical shape is fitted into the bed thus formed; this socket is provided at its cranial margin with at least two guide bushings for a drill running perpendicular to the plane of the socket mouth. Once the optimum position of the acetabular prosthesis to be implanted has been determined, for example by tilting or rotating the test prosthesis, the boreholes for accepting the screws 21 are drilled through the guide bushings. The test prosthesis is then removed and the length of the boreholes is measured. Using a countersink drill having a constant drilling depth, the peripheral sections of the boreholes are widened to accept the sliding sleeves 19 of the acetabular prosthesis 2. Then the actual acetabular prosthesis 2 of appropriate diameter is inserted in such a way that its sliding sleeves 19 come to rest in the recesses prepared for them. The prosthesis is firmly hammered into position and then fixed in place by means of the screws 21 of suitable length passing through the sliding sleeves 19. The sliding section 23 of the screws 21 must always project beyond the central end of the sliding sleeve 19.

The head prosthesis 1, which has in the meantime been got ready, is then inserted from the medial end, with the sliding component 9 being introduced first, into the bed which has been prepared for it in the bone and it is then hammered firmly into place. The peripheral end of the sliding component 9 should then end near the lateral opening of the sleeve 11. Once the head component 3 has been hammered onto the cone 4, the head component 3 is placed in the acetabular prosthesis 2 and the implantation process is complete.

Although the drawing depicts a hip endoprosthesis, the invention can, in principle, be applied with the same advantages to prostheses for other joints, in particular the knee joint. In all types of prosthesis the essential feature is that a joint part is slidingly guided in the axial direction in relation to an anchoring part, so that in the event of localized bone loss occurring, the parts of the prosthesis are prevented from tilting or twisting, without any interruption in the flow of forces through naturally existing bone structures.

In the area of the knee joint the anchoring component takes the form of one sliding sleeve implanted in the femoral shaft and another in the tibial shaft. A preferably rod-shaped sliding component securely connected to the femoral or tibial joint component, which may be of any suitable design, is slidingly located in this anchoring component.

In the shoulder area, the humeral anchoring component is fastened, in a manner similar to that used for the hip joint, to the lateral surface of the humerus. Again, a preferably rod-shaped sliding component, which is rigidly connected with a hemispherical joint component, is slidingly guided in this anchoring component. The glenoidal part of the prosthesis consists advantageously of a sleeve-shaped anchoring component which is fixed in the shoulder blade and in which a preferably rod-shaped sliding component, rigidly connected to a dish-shaped joint component, is slidingly guided.

I claim:

1. A hip joint prothesis comprising a hemispherical socket configured to be anchored in a recess of an acetabulum, the socket having a socket opening terminating at a peripheral rim and defining a plane at the rim, at least two elongated tubular guides each to be located at a cranial margin of the bone and having a longitudinal axis, means connecting the tubular guides to the socket and laterally of the socket opening so that their longitudinal axes are perpendicular to the plane of the socket opening, and fastening means having a proximal portion slidably disposed in the tubular guides and a distal portion for anchoring the socket to the bone.

2. A hip joint prosthesis according to claim 1 including a femoral head component for being slidably disposed in the socket, a neck member connected to the head component including a conical attachment surface having a vertex and facing away from the head for positioning against resected bone of the femur in substantial alignment with an axis of the femoral neck, an anchoring member for attachment to the femur and positioned laterally and distally of the femoral neck and including a tubular guide extending into the femur in alignment with the femoral neck axis, and an elongated guide member secured to the anchoring member, projecting coaxially with the femoral neck axis from the attachment surface and being slidably disposed in the tubular guide.

3. A hip joint prosthesis according to claim 2 wherein the conical attachment surface has a vertex angle of between 135° and 140°.

4. A hip joint prosthesis according to claim 2 wherein the anchoring member includes a tapered shaft projecting in a direction opposite to and coaxially with the guide member, and wherein the femoral head component includes a tapered bore adapted to receive the tapered shaft, the taper of the shaft and the bore being selected to secure the head component to the shaft.

* * * * *